US012722147B2

(12) United States Patent
Kim et al.

(10) Patent No.: US 12,722,147 B2
(45) Date of Patent: Sep. 1, 2026

(54) METHOD FOR PREPARING CATALYST FOR SELECTIVE HYDROGENATION OF CYCLODODECATRIENE AND CATALYST PREPARED BY PREPARATION METHOD

(71) Applicant: HANWHA SOLUTIONS CORPORATION, Seoul (KR)

(72) Inventors: Youngjin Kim, Daejeon (KR); Namjin Jang, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 527 days.

(21) Appl. No.: 18/257,322

(22) PCT Filed: Dec. 14, 2021

(86) PCT No.: PCT/KR2021/095124

§ 371 (c)(1), (2) Date: Jun. 14, 2023

(87) PCT Pub. No.: WO2022/131888

PCT Pub. Date: Jun. 23, 2022

(65) Prior Publication Data

US 2024/0033718 A1 Feb. 1, 2024

(30) Foreign Application Priority Data

Dec. 14, 2020 (KR) ........................ 10-2020-0174054

(51) Int. Cl.

| | |
|---|---|
| ***B01J 31/24*** | (2006.01) |
| ***B01J 31/28*** | (2006.01) |
| ***B01J 37/08*** | (2006.01) |
| ***C07C 5/05*** | (2006.01) |
| ***C07C 13/277*** | (2006.01) |

(52) U.S. Cl.

CPC ........... *B01J 31/2404* (2013.01); *B01J 37/08* (2013.01); *C07C 5/05* (2013.01); *C07C 13/277* (2013.01); *B01J 2231/646* (2013.01); *B01J 2531/821* (2013.01)

(58) Field of Classification Search

CPC .............. C07C 2523/46; C07C 2531/24; B01J 31/2404; B01J 2531/821; B01J 31/24; B01J 31/28

See application file for complete search history.

(56) References Cited

U.S. PATENT DOCUMENTS

| | | | | |
|---|---|---|---|---|
| 5,128,296 | A * | 7/1992 | Matson | B01J 31/1805 502/169 |
| 7,838,705 | B2 | 11/2010 | Teles | |
| 11,571,687 | B2 * | 2/2023 | Kim | C07C 5/05 |
| 2013/0096314 | A1 | 4/2013 | Kunz | |

FOREIGN PATENT DOCUMENTS

| | | | | |
|---|---|---|---|---|
| CN | 110790794 | A | 2/2020 | |
| EP | 3718993 | A1 | 10/2020 | |
| JP | 2000-169402 | A | 6/2000 | |
| KR | 10-2020-0076256 | A | 6/2020 | |
| WO | 2020130304 | A1 | 6/2020 | |
| WO | WO-2020130280 | A1 * | 6/2020 | C07C 7/04 |

OTHER PUBLICATIONS

T. Joseph, et al. 206, Journal of molecular catalysis A: Chemical, 13-21(2003)("Joseph") (Year: 2003).*

Selective hydrogenation of 1,5,9-cyclododecatriene to cyclododecene catalyzed by ruthenium complexes, Darryi R. Fahey et al., J. Org. Chem., vol. 38, No. 1, 1973.

Cationic mononuclear ruthenium carboxylates ascatalyst prototypes for self-induced hydrogenation of carboxylic acids, Masayuki Naruto et al.

Synthesis of RuH2(CO)(PPh3)3 in a $CO_2$ and $H_2$ atmosphere, Junzhong Zhang et al.

CN Office Action issued on Feb. 14, 2025.

Selective Hydrogenation of 1, 5, 9-Cyclododecatriene . . . .

The ESR issued on May 2, 2024.

Coordination Chemistry Reviews Dipak Kumar Dutta et al.

An office action issued on Sep. 14, 2023 for corresponding KR Patent Application.

The JP Office action issued on Jul. 23, 2024.

* cited by examiner

*Primary Examiner* — Alexander R Pagano
*Assistant Examiner* — Frank S. Hou
(74) *Attorney, Agent, or Firm* — Harvest IP Law, LLP

(57) ABSTRACT

The present invention relates to a method for preparing a catalyst for selective hydrogenation of cyclododecatriene and a catalyst prepared by the preparation method. The method for preparing a catalyst for selective hydrogenation of cyclododecatriene of the present invention includes: (S1) preparing a ruthenium complex by reacting ruthenium chloride with formaldehyde; and (S2) adding triphenylphosphine to the ruthenium complex and then allowing a reaction to proceed.

7 Claims, No Drawings

METHOD FOR PREPARING CATALYST FOR SELECTIVE HYDROGENATION OF CYCLODODECATRIENE AND CATALYST PREPARED BY PREPARATION METHOD

CROSS-REFERENCE TO RELATED APPLICATION(S)

This application is a National Stage of International Application No. PCT/KR2021/095124 filed on Dec. 14, 2021, claiming priority based on Korean Patent Application No. 10-2020-0174054 filed on Dec. 14, 2020, the disclosure of which is incorporated herein by reference in its entirety.

TECHNICAL FIELD

The present invention relates to a method for preparing a catalyst for selective hydrogenation of cyclododecatriene and a catalyst prepared by the preparation method.

BACKGROUND ART

Synthesis of cyclododecene (CDEN) by selective hydrogenation using cyclododecatriene (CDT) as a starting material has frequently been described in literature, and many studies have been conducted to increase a yield of cyclododecene.

In order for the selective hydrogenation to proceed, a metal ligand catalyst known as Wilkinson's catalyst, that is, a catalyst in which a ligand such as triphenylphosphine (TPP) or CO and a halogen atom bind to a metal such as ruthenium (Ru), rhodium (Rh), cobalt (Co), or nickel (Ni), has been used.

As such a catalyst plays a major role in the overall reaction, such as activating the entire reaction to proceed quickly or increasing a yield of a product without reacting by itself in selective hydrogenation, various catalyst-related studies have been conducted.

In U.S. Pat. No. 7,838,705, ruthenium chloride ($RuCl_3$), triphenylphosphine (TPP), formaldehyde, acetic acid, ethanol, and the like are added to a hydrogenation reactor for cyclododecatriene, and a ruthenium composite catalyst synthesized in an in-situ manner under hydrogenation conditions is used. Such a catalyst preparation method is intended to prepare a ruthenium composite catalyst capable of increasing a yield of cyclododecene, but as hydrochloric acid is produced as a by-product during a catalyst preparation process, and reaction residues such as methanol, water, and formaldehyde remain, a large amount of impurities is included in a product separated after selective hydrogenation.

In addition, in preparing the catalyst, as various solvents are used, it is difficult to manage and use the solvent, and thus the entire process is complicated.

DISCLOSURE

Technical Problem

An object of the present invention is to provide a method for preparing a catalyst for selective hydrogenation of cyclododecatriene that may prepare a high-purity catalyst by a simple process and implements a high catalyst production yield.

Another object of the present invention is to provide a catalyst for selective hydrogenation of cyclododecatriene that may produce cyclododecene with a high yield and high selectivity in a faster time when added in selective hydrogenation.

Technical Solution

In one general aspect, a method for preparing a catalyst for selective hydrogenation of cyclododecatriene includes: (S1) preparing a ruthenium complex by reacting ruthenium chloride with formaldehyde; and (S2) adding triphenylphosphine to the ruthenium complex and then allowing a reaction to proceed.

In the method for preparing a catalyst for selective hydrogenation of cyclododecatriene according to an exemplary embodiment of the present invention, the step (S1) may be performed at a temperature of 40° C. to 80° C.

In the method for preparing a catalyst for selective hydrogenation of cyclododecatriene according to an exemplary embodiment of the present invention, in the step (S1), a mole ratio of the ruthenium chloride to the formaldehyde may be 1:20 to 400.

In the method for preparing a catalyst for selective hydrogenation of cyclododecatriene according to an exemplary embodiment of the present invention, in the step (S1), a CO ligand may be formed by the reaction between the ruthenium chloride and the formaldehyde.

In the method for preparing a catalyst for selective hydrogenation of cyclododecatriene according to an exemplary embodiment of the present invention, the reaction in the step (S2) may be performed at a vaporization temperature of the formaldehyde.

In the method for preparing a catalyst for selective hydrogenation of cyclododecatriene according to an exemplary embodiment of the present invention, in the step (S2), a mole ratio of the ruthenium chloride to the triphenylphosphine added may be 1:1 to 300.

In the method for preparing a catalyst for selective hydrogenation of cyclododecatriene according to an exemplary embodiment of the present invention, in the step (S2), a $PPh_3$ ligand may be formed by the reaction between the ruthenium chloride and the triphenylphosphine.

In another general aspect, there is provided a catalyst for selective hydrogenation of cyclododecatriene prepared by the method described above.

In the catalyst for selective hydrogenation of cyclododecatriene according to an exemplary embodiment of the present invention, the catalyst may be added in an amount of 40 ppm to 200 ppm based on ruthenium with respect to cyclododecatriene in selective hydrogenation of cyclododecatriene.

The catalyst for selective hydrogenation of cyclododecatriene according to an exemplary embodiment of the present invention may be $RuH(PPh_3)_3COCl$.

Advantageous Effects

In the method for preparing a catalyst for selective hydrogenation of cyclododecatriene according to the present invention, a high-purity catalyst may be prepared with a high yield by a relatively simple process without using an additional solvent.

Since the catalyst prepared by the preparation method according to the present invention has excellent catalytic ability, when the catalyst is added and used in selective hydrogenation of cyclododecatriene, the reaction time for selective hydrogenation of cyclododecatriene may be shortened, and at the same time, cyclododecene may be produced with a high yield.

BEST MODE

Unless otherwise defined, all the technical terms and scientific terms used in the present specification have the same meanings as commonly understood by those skilled in the art to which the present invention pertains. The description for the known function and configuration unnecessarily obscuring the gist of the present invention will be omitted in the following description and the accompanying drawings.

In addition, unless the context clearly indicates otherwise, the singular forms used in the present specification may be intended to include the plural forms.

In addition, units used in the present specification without special mention are based on weight, and as an example, a unit of % or a ratio means wt % or a weight ratio. Unless otherwise defined, wt % means wt % of any one component in a composition with respect to the total weight of the composition.

In addition, a numerical range used in the present specification includes upper and lower limits and all values within these limits, increments logically derived from a form and span of a defined range, all double limited values, and all possible combinations of the upper and lower limits in the numerical range defined in different forms. Unless otherwise specifically defined in the specification of the present invention, values out of the numerical range that may occur due to experimental errors or rounded values also fall within the defined numerical range.

In the present specification, the expression "comprise(s)" is intended to be an open-ended transitional phrase having an equivalent meaning to "include(s)", "contain(s)", "have (has)", and "is (are) characterized by", and does not exclude elements, materials, or steps, all of which are not further recited herein.

In addition, the term "substantially" used in the present specification means that a specific element, material, or step that is not listed in combination with another element, material, or step may be present in an amount having no unacceptably significant influence on at least one basic and novel technical idea of the present invention.

The present invention relates to a method for preparing a catalyst for selective hydrogenation of cyclododecatriene, the method including: (S1) preparing a ruthenium complex by reacting ruthenium chloride with formaldehyde; and (S2) adding triphenylphosphine to the ruthenium complex and then allowing a reaction to proceed.

In the related art, ruthenium chloride ($RuCl_3$), triphenylphosphine (TPP), formaldehyde, acetic acid, ethanol, and the like have been added to a hydrogenation reactor for cyclododecatriene, and a ruthenium composite catalyst synthesized in an in-situ manner under hydrogenation conditions has been used. In such a catalyst preparation method, as hydrochloric acid is produced as a by-product during a catalyst preparation process, and reaction residues such as methanol, water, and formaldehyde remain, a large amount of impurities is included in a product separated after selective hydrogenation. In addition, in preparing the catalyst, as various solvents are used, it is difficult to manage and use the solvent, and thus the entire process is complicated.

However, in the present invention, a catalyst for selective hydrogenation of cyclododecatriene (CDT) may be prepared from ruthenium chloride, formaldehyde, and triphenylphosphine (TPP) by a relatively simple process without using an additional solvent. In addition, as by-products such as HCl are removed during the catalyst preparation process, there is no need for an additional separation process to obtain a high-purity catalyst, and the catalyst may be directly added to the selective hydrogenation of cyclododecatriene after preparation. Furthermore, in the present invention, the catalyst may be prepared with a high yield in preparing the catalyst, such that excellent process efficiency may be exhibited.

Furthermore, since the catalyst prepared by the preparation method according to the present invention has excellent catalytic ability, when the catalyst is added and used in selective hydrogenation of cyclododecatriene, the reaction time for selective hydrogenation of cyclododecatriene may be shortened, and at the same time, cyclododecene may be produced with a high yield.

Specifically, in the present invention, first, (S1) preparing a ruthenium complex by reacting ruthenium chloride with formaldehyde is performed. In this case, as ruthenium chloride ($RuCl_3$) reacts with formaldehyde ($CH_2O$), a CO ligand (carbonyl) may be formed. That is, the ruthenium complex may include a CO ligand and ruthenium.

The temperature in the step (S1) is not limited as long as it is in a range in which ruthenium chloride reacts with formaldehyde, but the step (S1) may be performed at a temperature of 40° C. to 80° C., and more preferably, 50° C. to 60° C. In the above range, ruthenium chloride reacts smoothly with formaldehyde within a relatively short time, such that a ruthenium complex may be prepared.

In addition, in the step (S1), the reaction may be performed for 10 minutes to 1 hour, and specifically, 20 minutes to 40 minutes, but the reaction time is not particularly limited as long as the reaction between ruthenium chloride and formaldehyde is completed.

In the step (S1), a mole ratio of the ruthenium chloride to the formaldehyde may be 1:20 to 400, specifically, 1:80 to 350, and more specifically, 1:100 to 150, but is not limited thereto. However, in the above range, the reaction is allowed to proceed smoothly in the step (S2) described below in a state where the ruthenium complex produced by the reaction between ruthenium chloride and formaldehyde is dissolved in formaldehyde. In addition, a ruthenium complex may be formed without consuming relatively expensive ruthenium chloride.

In the step (S1), ruthenium chloride may be in the form of a dark brown or black powder, formaldehyde may be pure formaldehyde or a formaldehyde aqueous solution, and the formaldehyde aqueous solution may have a concentration of 5 wt % to 40 wt %, but the present invention is not limited thereto.

The CO ligand is formed in the step (S1), the formation of the ruthenium complex may be seen through a change in color with the naked eye. As an example, when a ruthenium chloride powder is mixed with the formaldehyde solution, a reddish brown color is shown before the reaction, but a dark green color may be shown after the reaction.

In the present invention, after the step (S1), (S2) adding triphenylphosphine to the ruthenium complex and then allowing a reaction to proceed may be performed to prepare a catalyst for selective hydrogenation of cyclododecatriene. As the step (S2) is performed, a $PPh_3$ ligand may be formed by the reaction between the ruthenium complex and triphenylphosphine. That is, the prepared catalyst may contain the CO ligand and the $PPh_3$ ligand.

Specifically, through the step (S1), a non-uniform liquid mixture may be obtained by adding molten triphenylphosphine to formaldehyde in which a ruthenium composite is dissolved. In this case, the molten triphenylphosphine is triphenylphosphine melted at a melting point of 80° C. or higher, and may not be specifically limited as long as it is melted, but preferably, triphenylphosphine completely melted into a liquid state may be used. Thereafter, a catalyst for selective hydrogenation of cyclododecatriene may be prepared by reacting ruthenium composite with triphenylphosphine.

The reaction in the step (S2) may be performed at a vaporization temperature of the formaldehyde. The reaction between the ruthenium composite and the triphenylphosphine may be performed as formaldehyde vaporizes. The temperature is not limited as long as it is in a range in which formaldehyde vaporizes, and specifically, may be higher than a melting temperature of triphenylphosphine, and preferably, the step (S2) may be performed at a temperature of 80° C. to 200° C., and more preferably, 100° C. to 140° C. In the above range, residual formaldehyde, moisture, and methanol, which do not participate in the reaction in the step (S1), and HCl and the like produced in the step (S1) vaporize, and the ruthenium composite reacts with the triphenylphosphine smoothly within a relatively short time, such that a ruthenium complex may be produced within a short time.

In addition, in the step (S2), the reaction time is not limited as long as it is a time during which formaldehyde vaporizes completely.

In the step (S2), the amount of triphenylphosphine added may be based on the ruthenium chloride added in (S1). Specifically, a mole ratio of the ruthenium chloride to the triphenylphosphine added may be 1:1 to 300, and specifically, 1:4.5 to 230, but is not limited thereto. However, it is possible to prepare a catalyst having excellent catalytic ability within the above range.

In addition, the present invention relates to a catalyst prepared by the method described above, and hereinafter, the catalyst prepared by the method described above will be described in detail.

The catalyst prepared by the method described above is used for selective hydrogenation of cyclododecatriene, and may be represented by Chemical Formula $RuH(PPh_3)_3COCl$. Since the catalyst has excellent catalytic ability, when the catalyst is added and used in selective hydrogenation of cyclododecatriene, the reaction time for selective hydrogenation of cyclododecatriene may be shortened, and at the same time, cyclododecene may be produced with a high yield.

Specifically, in selective hydrogenation of cyclododecatriene, the catalyst of the present invention may be freely added as long as the reaction of the reactant may proceed sufficiently, and may be added in an amount of 40 ppm to 200 ppm, and specifically, 50 ppm to 150 ppm, based on ruthenium with respect to cyclododecatriene. The catalyst may have excellent catalytic ability compared to the amount of catalyst added within the above range, and thus, cyclododecene (CDEN) may be efficiently produced from cyclododecatriene.

In addition, the selective hydrogenation of cyclododecatriene to which the catalyst of the present invention is added may be performed under conditions of a temperature of 100 to 200° C. and a pressure of 10 to 80 bar, preferably under conditions of a temperature of 140 to 180° C. and a pressure of 20 to 60 bar, and more preferably under conditions of a temperature of 150 to 175° C. and a pressure of 20 to 40 bar, but it is only a preferred example for improving the yield of cyclododecene, and the present invention is not limited thereto.

Hereinafter, the method for preparing a catalyst for selective hydrogenation of cyclododecatriene according to the present invention will be described in more detail with reference to Examples. However, the following Examples are only reference examples for describing the present invention in detail, and the present invention is not limited thereto and may be implemented in various forms.

Unless otherwise defined, all technical terms and scientific terms used herein have the same meaning as commonly understood by those skilled in the art to which the present invention pertains. The terms used for the description herein are only intended to effectively describe a certain Example and are not intended to limit the present invention. In addition, unless otherwise stated in the specification, a unit of an additive may be wt %.

Example 1

A reaction solution was prepared by dissolving 1.0 g of $RuCl_3$ in 119.7 g of formaldehyde (37% formaldehyde aqueous solution), and then a reaction was allowed to proceed at 60° C. for 30 minutes. After confirming that the color of the reaction solution was changed from reddish brown to dark green, 3.27 g of triphenylphosphine (TPP) completely melted at 100° C. was added and mixed, and then residual formaldehyde was evaporated at 100° C., thereby preparing a catalyst.

Example 2

A catalyst was prepared in the same manner as that of Example 1, except that triphenylphosphine (TPP) was used in an amount of 4.91 g instead of 3.27 g.

Example 3

A catalyst was prepared in the same manner as that of Example 1, except that triphenylphosphine (TPP) was used in an amount of 205.7 g instead of 3.27 g.

Experimental Examples

In order to evaluate the catalytic ability in each of Examples, the catalyst was added in the selective hydrogenation of cyclododecatriene, and then the reaction time, conversion, selectivity to cyclododecene, and yield were measured.

The addition conditions of each of Examples are shown in Table 1. At this time, TPP of each of Examples was fixed so that the total amount of TPP included in the catalyst was 230 times that of Ru. In Comparative Examples, the amount of CDT added (mol) was the same as that in each of Examples, and 0.08 g of $RuCl_3$, 9.58 g of formaldehyde (37% formaldehyde aqueous solution), and 20.0 g of TPP were added in an in-situ manner.

TABLE 1

| Classification | Example 1 | Example 2 | Example 3 |
|---|---|---|---|
| Amount of catalyst mixture added (Ru:TPP mole ratio) | 0.317(1:3) | 0.448(1:4.5) | 20.1(1:230) |
| TPP (mole ratio to Ru) | 19.8 (227) | 19.7 (225.5) | 0 (0) |
| Amount of CDT added (mole ratio) | 400 | 400 | 400 |

The reaction solution was stirred under a condition of hydrogen at 6 bar, and then selective hydrogenation was performed for 2 hours under a condition in which 180° C. and bar were maintained, and at this time, the reaction was performed in a stirred tank reactor equipped with a gas-induced hollow stirrer. The selective hydrogenation was performed for 1.5 hours, and then the reaction solution after cooling to 30° C. or lower under nitrogen conditions was recovered.

The conversion was calculated by the following Calculation Formula 1, the selectivity was calculated by the following Calculation Formula 2, and the yield was calculated by the following Calculation Formula 3. The results thereof are shown in Table 2.

$$\text{Conversion (\%)} = (CDT0 - CDT1 - CDDN1)/CDT0 \times 100 \qquad \text{[Calculation Formula 1]}$$

In Calculation Formula 1, CDT0 is the number of moles of cyclododecatriene added, CDT1 is the number of moles of cyclododecatriene after reaction, and CDDN1 is the number of moles of cyclododecadiene. In this case, cyclododecadiene (CDDN) is a product obtained in unfinished hydrogenation in which only one double bond of three double bonds of cyclododecatriene is hydrogenated and two double bonds remain.

$$\text{Selectivity (\%)} = CDEN1/(CDEN1 + CDAN1) \times 100 \qquad \text{[Calculation Formula 2]}$$

In Calculation Formula 2, CDEN1 is the number of moles of cyclododecene produced, and CDAN1 is the number of moles of cyclododecane, which is a by-product produced.

$$\text{Yield (\%)} = \text{Conversion} \times \text{Selectivity} \qquad \text{[Calculation Formula 3]}$$

TABLE 2

| Classification | Example 1 | Example 2 | Example 3 | In-situ (Comparative Example) |
|---|---|---|---|---|
| TPP/Ru (mole ratio) | | | 230 | |
| Reaction time (h) | 1.5 | 1.5 | 1.5 | 1.5 |
| Conversion (%) | 98.2 | 98.7 | 99.0 | 93.4 |
| Selectivity to CDEN (%) | 98.2 | 98.0 | 98.0 | 98.8 |
| Yield (%) | 96.4 | 96.7 | 97.0 | 93.2 |

Referring to Table 2, it was confirmed that, in the case of using the catalyst of the present invention, cyclododecene was produced with high conversion and selectivity similar to those in Comparative Examples, and cyclododecene was produced with a high yield in a short reaction time compared to Comparative Examples. Hereinabove, although the present invention has been described by specific matters, limited exemplary embodiments, and drawings, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the described exemplary embodiments, but the claims and all modifications equal or equivalent to the claims are intended to fall within the spirit of the present invention.

The invention claimed is:

1. A method for preparing a catalyst for selective hydrogenation of cyclododecatriene, the method comprising:

(S1) preparing a ruthenium complex by reacting ruthenium chloride with formaldehyde without other solvent; and (S2) adding triphenylphosphine to the ruthenium complex and then allowing a reaction to proceed and removing by-products wherein, the step of S1 and the step of S2 are two separate steps.

2. The method of claim 1, wherein the step (S1) is performed at a temperature of 40° C. to 80° C.

3. The method of claim 1, wherein in the step (S1), a mole ratio of the ruthenium chloride to the formaldehyde is 1:20 to 400.

4. The method of claim 1, wherein in the step (S1), a CO ligand is formed by the reaction between the ruthenium chloride and the formaldehyde.

5. The method of claim 1, wherein the reaction in the step (S2) is performed at a vaporization temperature of the formaldehyde.

6. The method of claim 1, wherein in the step (S2), a mole ratio of the ruthenium chloride to the triphenylphosphine added is 1:1 to 300.

7. The method of claim 1, wherein in the step (S2), a $PPh_3$ ligand is formed by the reaction between the ruthenium complex and the triphenylphosphine.

* * * * *